United States Patent [19]

Mattler

[11] E Re. 30,365

[45] Reissued Aug. 12, 1980

[54] DISPOSABLE CATHETER

[76] Inventor: Martin Mattler, 24575 Franklin Park Dr., Franklin, Mich. 48025

[21] Appl. No.: 681,511

[22] Filed: Apr. 29, 1976

Related U.S. Patent Documents

Reissue of:

[64] Patent No.: 3,896,816
Issued: Jul. 29, 1975
Appl. No.: 360,363
Filed: May 14, 1973

U.S. Applications:

[63] Continuation-in-part of Ser. No. 139,725, May 3, 1971, abandoned.

[51] Int. Cl.[2] ..... A61M 25/00

[52] U.S. Cl. ..... 128/349 B; 128/246

[58] Field of Search ..... 128/1 R, 239–241, 128/245, 246, 248, 251, 325, 344, 348–351, DIG. 26

[56] References Cited

U.S. PATENT DOCUMENTS

| | | | |
|---|---|---|---|
| 1,167,979 | 1/1916 | Clark | 128/245 |
| 2,046,094 | 6/1936 | Schmidt | 128/349 R |
| 2,330,399 | 9/1943 | Winder | 128/349 B |
| 2,457,244 | 12/1948 | Lamson | 128/246 |
| 2,687,131 | 8/1954 | Raiche | 128/349 B |
| 2,865,373 | 12/1958 | Recker | 128/239 |
| 2,936,760 | 5/1960 | Gants | 128/349 B |
| 3,049,125 | 8/1962 | Kriwkowitsch | 128/325 |
| 3,137,299 | 6/1964 | Tabor | 128/351 |
| 3,459,175 | 8/1969 | Miller | 128/246 X |

*Primary Examiner*—Dalton L. Truluck
*Attorney, Agent, or Firm*—Irving M. Weiner; Pamela S. Burt; Melvin Yedlin

[57] ABSTRACT

A catheter formed of an elongated, hollow tube having a sealed, separate air passageway formed integrally of the tube and extending from a point near the forward end of the tube to an integral air inlet nozzle located near the rear end of the tube and extending outwardly therefrom. An inflatable barrel shaped cuff is mounted upon and encircles the tube near its forward end, there being an opening in the tube wall communicating the interior of the cuff with the air passageway for inflating and deflating the cuff. A cup shaped seal is also mounted upon the tube and is frictionally secured thereto by integral springy flanges which permit forwardly sliding the seal upon the tube but which resists rearward sliding of the seal.

3 Claims, 10 Drawing Figures

FIG. 4
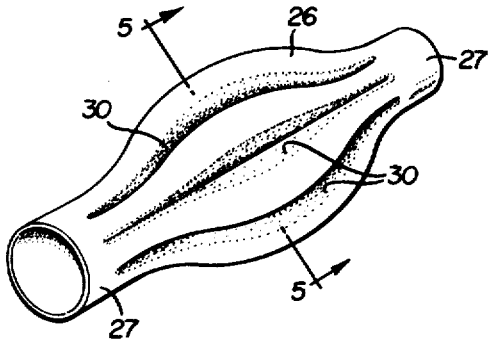
FIG. 5
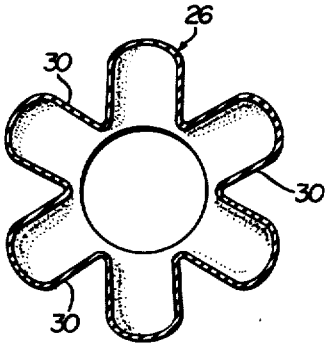
FIG. 6
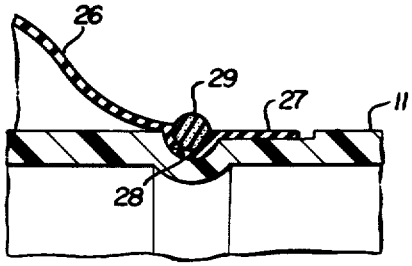
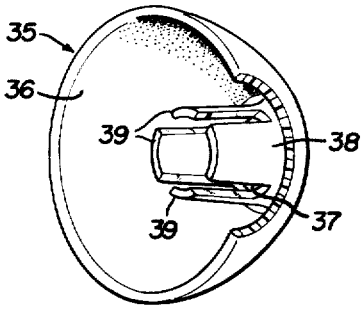
FIG. 7
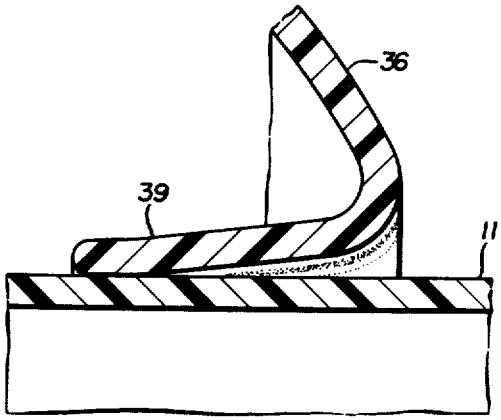
FIG. 8

DISPOSABLE CATHETER

Matter enclosed in heavy brackets [ ] appears in the original patent but forms no part of this reissue specification; matter printed in italics indicates the additions made by reissue.

CROSS-REFERENCE TO RELATED APPLICATIONS

This application is a continuation-in-part application of copending U.S. Pat. application Ser. No. 139,725, filed May 3, 1971, for "Disposable Catheter," now abandoned.

BACKGROUND OF THE INVENTION

Catheters generally comprise an elongated tube for insertion into a body cavity and an inflatable cuff or sealing device for sealing against the body cavity opening around the tube to prevent fluid leakage around the tube. An example of such a catheter is found in my prior U.S. Pat. No. 3,417,753 granted Dec. 24, 1968.

In the past, catheters, along with other medical appliances, were reused and sterilized after each use. However, due to the difficulties of sterilization and the expenses of labor in connection with any cleaning and resterilizing of medical appliances, efforts have been made to make many medical appliances disposable, that is, single use. This is particularly true with regard to catheters primarily designed for insertion into anal cavities. It has been medically proven that it is impossible to provide that degree of sterilization of anal catheters necessary to prevent the transference of pathogens from one patient or user to another. Thus, anal catheters must be disposable. This means, that the construction must be so inexpensive that is more economical to throw away the appliance rather than to clean and reuse it. However, the appliance must be made well so that it functions properly on its first and only use.

The foregoing patent illustrates an example of a catheter made for single use. However, it is desirable to make improvements upon such catheter particularly to reduce its overall diameter and to eliminate tubes or other items which are separate from the basic catheter tube, in order to facilitate ease of entry into and withdrawal out of the body cavities. Thus, the invention herein relates to a disposable or single use catheter which is an improvement over prior catheters.

SUMMARY OF THE INVENTION

The invention herein relates to a disposable or single use catheter formed of a tube having an integral, internal air passageway which utilizes only a small portion of the cross-section of the tube. The tube carries a barrel shaped inflatable cuff of normally small diameter, but which may be easily inflated into an adequate diameter for sealing against the wall of a body cavity, around the tube. The tube also carries a separate slidable plastic shield for sealing against the body area defining the opening within which the catheter tube is inserted. The shield includes means for facilitating placement thereof on the exterior of the tube or shank.

The tube also has means for positive stop positioning formed on the exterior thereof. The catheter also includes means for facilitating fluid flow into a body cavity through the head of the tube.

The invention herein contemplates forming the catheter tube with its barrel-shaped cuff of simple and inexpensive construction, while at the same time having the structural strength and configuration to adequately perform its function.

These and other objects and advantages of this invention will become apparent upon reading the following description of which the attached drawings form a part. In the drawing like reference characters refer to like parts throughout the several views in which:

BRIEF DESCRIPTION OF THE DRAWINGS

FIG. 4 is a perspective view of the inflatable cuff;

FIG. 5 is a cross-sectional view taken in the direction of arrows 5—5 of FIG. 4 of the cuff;

FIG. 6 is a fragmentary view showing the connection or sealing between the cuff and the tube;

FIG. 7 is a perspective view of the cup-shaped, external shield;

FIG. 8 is an enlarged, fragmentary view of the means for mounting the shield upon the catheter tube;

DESCRIPTION OF THE PREFERRED EMBODIMENTS

In copending U.S. Patent application Ser. No. 139,725, the disclosure of which is hereby incorporated by reference, there is described a first embodiment of the present invention, and is detailed in FIGS. 1–8, hereof.

Figure 1:
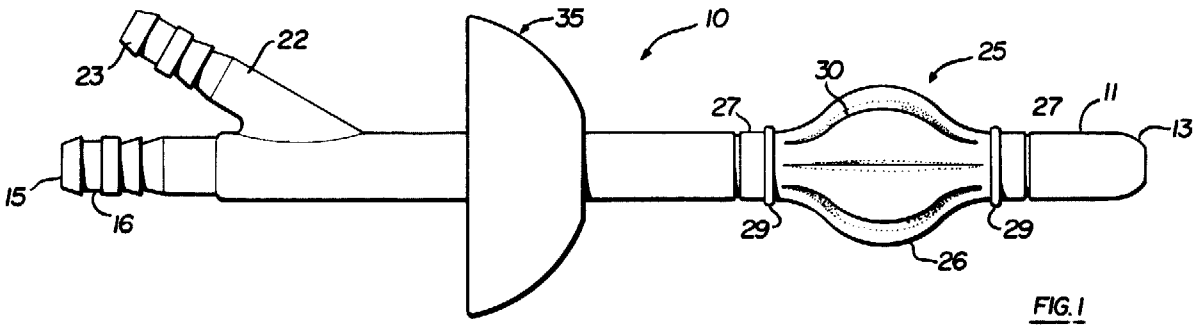
FIG. 1 is an elevational view of a catheter assembly.
Figure 2:
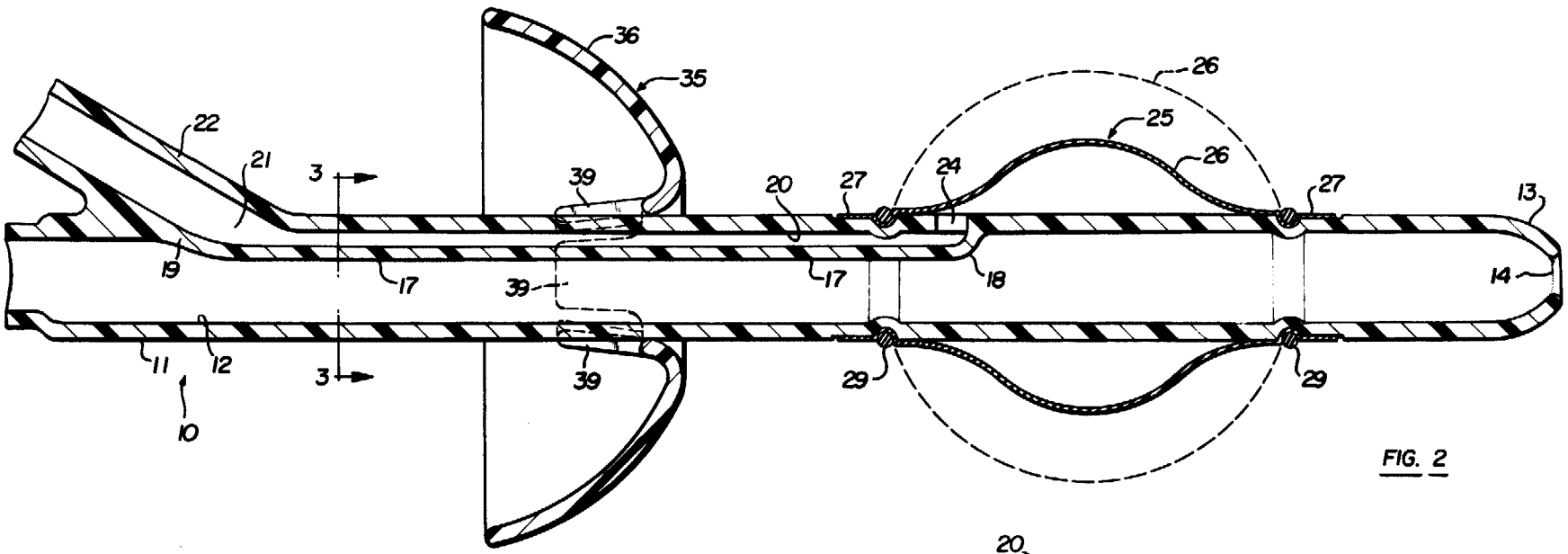
FIG. 2 is an enlarged, fragmentary cross-sectional view of a catheter assembly.

FIGS. 1 and 2 illustrate the catheter assembly 10 of the first embodiment and which includes an elongated, thin wall, hollow tube 11, formed of a suitable plastic material. The central opening of the tube forms a fluid passageway 12 which extends from the forward rounded or bulbous end or head 13 through which it opens at 14, to the rear or opposite end 15 of the tube 11. The rear end of the tube is formed with a suitable hose grip configuration 16 over which a conventional rubber-like hose (not shown) may be slipped and frictionally engaged and retained in place.

Figure 3:
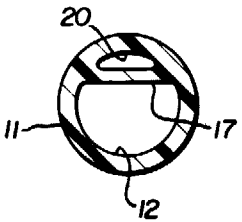
FIG. 3 is a cross-sectional view of the catheter tube, taken in the direction of arrows 3—3 of FIG. 2.

As shown in FIGS. 2 and 3 a transversely arranged, longitudinally extending internal flat strip 17 is integrally formed within the tube 11. The strip 17 is closely adjacent to a segment of the tube wall, as shown, with the long edges of the strip integral with the wall. The forward end 18 of the strip 17 is integral with the tube wall near the forward end of the tube. Likewise, the rear end 19 of the strip 17 is integral with the tube wall near the rear end 15 of the tube. Thus, the strip, in conjunction with a segment of the wall of the tube, defines a closed air passageway 20 which, as illustrated in FIG. 3, occupies a relatively minor portion of the cross-section of the interior of the tube, so that the major portion of the interior cross-section is unobstructed for fluid passage through the passageway 12.

The air passageway 20 opens at 21 into an integral air nozzle 22 which extends angularly outwardly of the tube near its rear end 15. A hose grip configuration 23 (FIG. 1) is formed on the end of the air nozzle 22 so that a rubber-like tube or other suitable hosing (not shown)

may be slipped over and frictionally gripped upon the nozzle 22. The hosing is attached at its other end to a source of compressed air (not shown) which delivers or supplies compressed air into the air passageway 20. As is described hereinafter, the compressed air is employed to inflate a suitable cuff which aids fluid retention in a body cavity.

Referring to FIG. 2, air opening 24 is formed in the tube wall at the forward end of the air passageway 20. The area around the air opening 24 is covered by an inflatable cuff 25. The cuff 25 is, preferably, formed of an air impervious, inflatable, resilient and flexible material, such as latex or a rubber-like material. In the embodiment shown in FIGS. 1–8, the cuff 25 has a central barrel-shaped portion 26 and integral, opposed short cylinder end portions 27. Annular grooves 28 (FIG. 6) are formed in the tube wall beneath the cuff cylinder portions 27, O-rings or O-ring seals 29 are provided to surround the cylinder portions 27 and to be positioned over the grooves 28. The seals 29 frictionally anchor and seal the cylinder portions to the tube wall 11.

The barrel-shaped portion 26 of the cuff 25 is provided with a plurality of inwardly directed pleats or flutes 30 (see FIG. 5). These pleats 30 extend the full length of the barrel-shaped portion 26. They invert when the cuff is inflated to permit the relatively small diameter uninflated cuff 25 to expand into a substantial inflated diameter.

As best depicted in FIGS. 2 and 7, for sealing against the body portion surrounding the entry to a body cavity, a shield 35 is mounted upon the tube 11. The shield 35 is mounted below the cuff 25 and engages the body portion surrounding the cavity. The shield 35 is rearwardly and outwardly curved, relative to the tube 11, and forms a cup shape portion 36. The shield 35 has central opening 37 surrounded by a rearwardly directed hub portion 38 through which the tube 11 is closely fitted. Springy fingers or flanges 39 integral with the hub 38 extend rearwardly therefrom. The flanges 39 frictionally engage and grip against the tube 11. The shield is formed of a springy, relatively flexible plastic material which, while being stiff enough to maintain its normal shape, may be sufficiently bent and flexed to conform more closely to the body portion against which it engages.

The spring fingers or flanges 39 are tapered inwardly relative to the axis of the tube to frictionally grip against the tube wall, as illustrated in FIG. 8. Thus, the shield may be easily slid towards the forward end or head of the tube but resists sliding backwards towards the rear end of the tube due to the increase in frictional engagement between the fingers or flanges and the tube wall.

Figure 9:
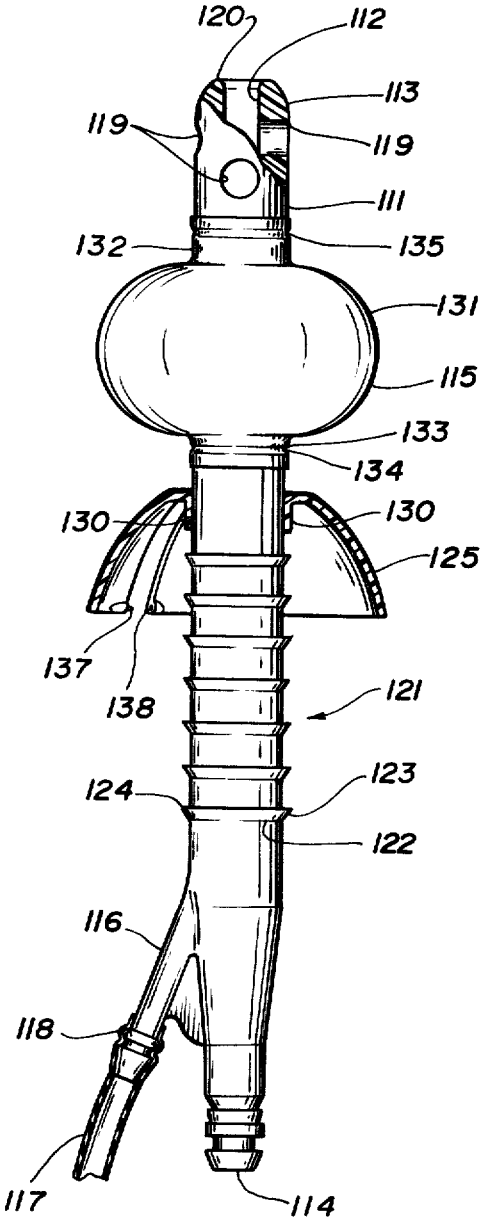
FIG. 9 is a side elevational view of an alternate embodiment of a catheter tube.
Figure 10:
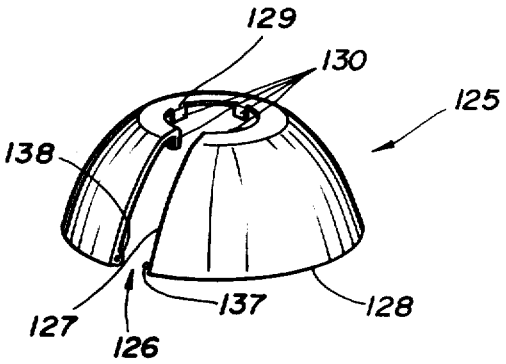
FIG. 10 is a perspective view of an alternate embodiment of the external shield.

Referring now to FIGS. 9 and 10, there is depicted therein an alternate embodiment of the present invention. In this embodiment there is provided an elongated tube or shank 111 having a central fluid passageway 112. The passageway 112 extends from the forward end or head 113 of the tube 111 to the rearward end 114 of the tube. The internal configuration of the tube is the same as hereinabove described including the air passageway in communication with a cuff 115 through an air nozzle 116. A hose 117 is connected to the nozzle 116 and is gripped thereonto by suitable gripping means 118. The gripping means 118 is analogous to the grip configurations 23 and 16 of the hereinbefore described embodiment.

The hose 117 is connected at its other end to a source of compressed air or the like (not shown) for inflating the cuff 115 through the air passageway.

In order to facilitate fluid flow through the fluid passageway and in accordance with the present embodiment a plurality of fluid delivery apertures 119 are circumferentially disposed about the tube 111 proximate the head 113. A central fluid delivery apertures 120 is also provided at the terminus of the fluid passageway 112. By providing a plurality of fluid delivery apertures 119, 120, the fluid flow pressure of the fluid exiting from the tube is greatly decreased. Concomitantly a greater volume of fluid can be introduced into a body cavity with less discomfort to the body.

As shown in FIG. 9, the tube 111 has formed on the exterior thereof positive stop positioning means 121. The positive stop positioning means generally comprise at least one forwardly directed bead 122. The bead 122 tapers outwardly from the tube 111, as at 123, and thereby defines a ledge 124 which extends circumferentially around the tube 111.

The ledge 124, acts as a barrier to limit or retard any motion of the shield 125 toward the rear 114 of the tube 111 in a manner described subsequently. The bead 122 may be integrally formed, such as by molding or the like, or otherwise affixed to the exterior of the tube 111 in the medial portion thereof. A plurality of beads 122 are provided to accommodate varying placements of the shield 125.

In the present embodiment of the invention and as shown in FIG. 10, the shield 125 also includes means 126 for mounting the shield on the tube 111. The means 126 generally comprises an elongated slot or cut-out portion 127. The slot 127 is provided along the cup-shaped portion 128 as well as through the hub portion 129.

Because of the materials used to manufacture the shield, the mounting thereof is facilitated by the slot 127. The slot affords flexure of the shield to enable its mounting either between two beads, or between a bead and the cuff 115. The resiliency of the shield maintains its frictional mounting on the tube. In order to insure that the shield remains locked around the tube means 136 are provided. The means 136 generally comprises a male-female coupling 137, 138 formed on the interior surface of the cup-shaped portion of the shield 127 proximate the area of the slot 127. Preferably, the coupling 137, 138 is a detente arrangement which functions in a known manner. Because of the flexibility of the shield engagement and interlocking of the coupling 137, 138 is possible. Moreover, by interlocking the shield any possibility of the shield flexing and sliding off the tube is prevented. In all other respects, the shield 125 is the same as the shield 35 hereinbefore described.

It is seen that, in accordance with this embodiment of the invention, if the shield 125 moves toward the rear 114 of the tube 111, the flanges 130 of the shield 125 will abut and engage a ledge 124 to prevent any movement of the shield therepast, thus providing positive stop positioning of the shield.

Because the catheter hereof is primarily intended for insertion into an anal cavity, the shield provides two important functions. First, the shield functions as a safety means to prevent and inhibit premature fluid leakage out of the anal cavity. Secondly, the shield functions as a safety stop if the cuff is improperly positioned or if the user or patient attempts to expel the cuff with internal pressure. Thus, the shield is critical to the overall efficacy and efficiency of the present catheter.

Referring again to FIG. 9, the cuff 115 used herein can comprise the fluted cuff 25 heretofore described or any other suitably configured cuff. In the embodiment of FIG. 9, the cuff 115 includes a central toroidal portion 131 and integrally formed opposed elongate portions 132 and 133, respectively. The elongate portion 133 can be inverted within the toroidal portion 131 and clamped in the annular groove 134 through an O-ring seal, as hereinbefore described.

Similarly, the elongate portion 132 can be clamped in the annular groove 135 through an O-ring seal (now shown).

It is to be understood though, that the heretofore described fluted cuff can be used with equal efficacy in this embodiment and vice versa.

It will be appreciated by those skilled in the art, that with the present invention there is provided means for facilitating fluid flow, means for mounting the shield, and means for positive stop positioning the shield, all of which facilitate the use and deployment of a disposable catheter.

OPERATION

In operation, a rubber hose is assembled to the rear end configuration of the tube for the passage of fluids. A separate rubber hose or tube is connected to the air nozzle, frictionally engaging the grip portion 23 of the nozzle. Air is pumped through the air passageway by means of a suitable hand pump or the like, to inflate the barrel-shaped or toroidal portion of the cuff. This is done after the catheter tube is inserted into the body cavity the required distance. Thereafter, the shield 35 is slid towards, against and into snug contact with the body portion surrounding the entrance to the body cavity where it functions to limit the leakage of fluid around the outside of the tube. The shield resists sliding backwards and remains in place after contacting the body portion and is aided and abetted by the positive stop positioning means. For removal, air is permitted to escape out of the nozzle to deflate the cuff, and the tube is withdrawn from the body cavity.

With the foregoing construction, the cuff inflates uniformly and symmetrically about its center axis, with its wall thickness remaining uniform. This is an improvement over the prior catheters which have a tendency to inflate non-symmetrically and with corresponding bulges and non-uniform wall thicknesses.

Having fully described an operative embodiment of this invention I now claim:

1. A catheter comprising:

an elongated hollow tube having a forward end and a rearward end, the forward end being provided with a plurality of apertures to facilitate fluid delivery to a body cavity, a first opening in the tube wall proximate the forward end thereof, a sealing cuff mounted upon the tube over the area including the first opening, the sealing cuff comprising a thin walled, air impervious, resilient rubber-like material, the tube extending through the cuff and the cuff end portion being sealed to the tube such that the cuff may be inflated to an enlarged ring-shape co-axial with the tube for sealing a body cavity within which the tube is inserted;

a second opening in the tube wall near the rearward end thereof;

means disposed within the tube for interconnecting the first and second openings, a rearwardly and outwardly curved shield mounted below the cuff for sealing the body cavity, the shield including a central opening and having a rearwardly directed hub portion through which the tube is fitted, a plurality of fingers integrally formed with the hub and extending rearwardly therefrom, the fingers permitting forward sliding of the shield while resisting rearward movement of the shield, means for mounting the shield on the tube, the mounting means including an elongated slot provided through the shield and a coupling means for closing the slot, positive stop positioning means formed on the exterior of the tube, the means comprising at least one forwardly directed bead tapering outwardly from the tube, and wherein the openings and the means for interconnecting the openings cooperate to define an air inlet for flowing pressurized air into and for discharging air from the cuff to inflate and deflate, respectively, the cuff after the tube is inserted into the body cavity.

*2. A catheter comprising:*

*an elongated hollow tube having a forward end and a rearward end, the forward end being provided with a plurality of apertures to facilitate fluid delivery to a body cavity;*

*a first opening in the tube wall proximate the forward end thereof;*

*a sealing cuff mounted upon the tube over the area including the first opening, the sealing cuff comprising a thin walled, air impervious, resilient rubber-like material;*

*the tube extending through the cuff and the cuff end portion being sealed to the tube such that the cuff may be inflated to an enlarged ring-shape co-axial with the tube for sealing a body cavity within which the tube is inserted;*

*a second opening in the tube wall near the rearward end thereof;*

*means disposed within the tube for interconnecting the first and second openings;*

*said sealing cuff comprising a cuff central portion with integral, co-axially aligned, short, opposite cylindrically-shaped cuff end portions;*

*upon deflation of said sealing cuff, the circumference of said cuff central portion of said sealing cuff is only slightly greater than the circumference of the major portion of said elongated hollow tube;*

*said sealing cuff has at least one fold therein which inverts when said sealing cuff is inflated to permit the relatively small diameter uninflated sealing cuff to expand to a substantial inflated diameter;*

*a rearwardly and outwardly curved shield mounted below the cuff for sealing the body cavity, the shield including a central opening and having a hub portion through which the tube is fitted;*

*means for mounting the shield on the tube, the mounting means including an elongated slot provided through the shield and a coupling means for closing the slot; and wherein* the openings and the means for interconnecting the openings cooperate to define an air inlet for flowing pressurized air into and for discharging air from the cuff to inflate and deflate, respectively, the cuff after the tube is inserted into the body cavity.

*3. A catheter according to claim 2, wherein:*

*said shield is disposed between said sealing cuff and said second opening in said tube wall; and*

*said shield has an outer surface which faces said sealing cuff and which has substantially the shape of a surface of revolution.*

* * * * *